United States Patent
Strong

(10) Patent No.: US 10,219,955 B2
(45) Date of Patent: Mar. 5, 2019

(54) FLEXIBLE MANUFACTURING AND ARTICLE ARRAYS FROM THE SAME

(71) Applicant: The Procter & Gamble Company, Cincinnati, OH (US)

(72) Inventor: Kevin Charles Strong, Loveland, OH (US)

(73) Assignee: The Procter & Gamble Company, Cincinnati, OH (US)

(*) Notice: Subject to any disclaimer, the term of this patent is extended or adjusted under 35 U.S.C. 154(b) by 582 days.

(21) Appl. No.: 14/721,187

(22) Filed: May 26, 2015

(65) Prior Publication Data
US 2015/0351975 A1 Dec. 10, 2015

Related U.S. Application Data

(60) Provisional application No. 62/008,524, filed on Jun. 6, 2014.

(51) Int. Cl.
*A61F 13/15* (2006.01)
*A61F 13/20* (2006.01)
(Continued)

(52) U.S. Cl.
CPC ........ *A61F 13/266* (2013.01); *A61F 13/2082* (2013.01); *A61F 13/2085* (2013.01);
(Continued)

(58) Field of Classification Search
CPC .............. A16F 13/5519; A61B 12/006; A61F 13/2082; A61F 13/2085; A61F 13/2097;
(Continued)

(56) References Cited

U.S. PATENT DOCUMENTS 5,084,038 A * 1/1992 Sheldon .............. A61F 13/2082
156/193
5,519,930 A * 5/1996 Sengstock ........... A61F 13/2085
29/281.1
(Continued)

FOREIGN PATENT DOCUMENTS

WO    WO 2008/008794 A2    1/2008

OTHER PUBLICATIONS

PCT International Search Report, dated Aug. 10, 2015, 127 pages.
U.S. Appl. No. 14/737,538, filed Jun. 12, 2015, Strong, et al.

*Primary Examiner* — Michele M Kidwell
(74) *Attorney, Agent, or Firm* — Andres E. Velarde; Andrew J. Hagerty

(57) ABSTRACT

Methods and apparatuses for manufacturing multiple different articles are provided. One apparatus embodiment includes a first intravaginal article assembly module; a second intravaginal article assembly module; and an applicator module capable of receiving and handling applicators suitable for both first intravaginal articles from the first intravaginal article assembly module and second intravaginal articles from the second intravaginal article assembly module. The apparatus only operates with one of the first intravaginal article assembly module and the second intravaginal article assembly module at one time. The first intravaginal articles are absorbent articles and the second intravaginal articles are non-absorbent articles.

9 Claims, 9 Drawing Sheets

(51) Int. Cl.
    *A61F 13/26* (2006.01)
    *A61F 13/551* (2006.01)
    *A61F 6/08* (2006.01)

(52) U.S. Cl.
    CPC ...... *A61F 13/2097* (2013.01); *A61F 13/5519* (2013.01); *A61F 6/08* (2013.01); *Y10T 29/49828* (2015.01)

(58) Field of Classification Search
    CPC ...... A61F 13/266; A61F 13/5519; A61F 6/08; Y10T 29/49828
    See application file for complete search history.

(56) References Cited

U.S. PATENT DOCUMENTS

| | | | |
|---|---|---|---|
| 6,574,520 B1 | 6/2003 | Liu et al. | |
| 6,925,784 B2 | 8/2005 | Escobar et al. | |
| 8,361,045 B2 * | 1/2013 | Thorson | A61F 13/15804 604/367 |
| 2011/0184331 A1 | 7/2011 | Minoguchi et al. | |
| 2011/0247199 A1 * | 10/2011 | LaVon | A61F 13/15585 29/650 |
| 2014/0000629 A1 | 1/2014 | Durling et al. | |
| 2014/0100417 A1 | 4/2014 | Durling et al. | |

* cited by examiner

FLEXIBLE MANUFACTURING AND ARTICLE ARRAYS FROM THE SAME

FIELD OF THE INVENTION

The present invention relates to methods and apparatuses for manufacturing multiple different articles. The present invention also relates to arrays of different articles. And the present invention relates to manufacturing methods that utilize an article carrier system wherein the carriers are independently moveable.

BACKGROUND OF THE INVENTION

Today, many different kinds of disposable absorbent articles are being manufactured on a plurality of unique machines. Disposable absorbent articles are currently being manufactured and sold for use by infants, toddlers and adults. Such disposable absorbent articles include infant diapers, child training pants, menstrual pants, adult incontinence undergarments, guards for men, briefs, etc. Many machines are limited to producing a distinct disposable absorbent article in a particular size. Some machines can be retrofitted or modified to produce a smaller or larger size disposable absorbent article but the machines cannot easily be retrofitted to produce disposable articles that are different beyond just their size.

U.S. Pat. No. 8,361,045 discloses apparatuses and methods to address the above challenge. This patent specifically discloses apparatuses and methods for manufacturing several distinct disposable absorbent articles on a single machine. The '045 patent discloses a single machine that begins with a fundamental building block of absorbent material with flexibility downstream to form different disposable absorbent articles. But the '045 patent fails to teach apparatuses and methods for manufacturing multiple different articles wherein one of the articles is an absorbent article and another of the articles is a non-absorbent article (that does not build upon the initial fundamental building block of absorbent material).

There is still a need for machines and methods that can produce a disposable absorbent article and a disposable non-absorbent article. At least some of the embodiments of the present invention address this need.

SUMMARY OF THE INVENTION

The present invention relates to methods and apparatuses for manufacturing multiple different articles. In accordance with one embodiment, there has now been provides a multi-article manufacturing apparatus, comprising: a first intravaginal article assembly module; a second intravaginal article assembly module; and an applicator module capable of receiving and handling applicators suitable for both first intravaginal articles from the first intravaginal article assembly module and second intravaginal articles from the second intravaginal article assembly module. The apparatus only operates with one of the first intravaginal article assembly module and the second intravaginal article assembly module at one time. The first intravaginal articles are absorbent articles and the second intravaginal articles are non-absorbent articles.

In accordance with a second embodiment, there has now been provides a multi-article manufacturing apparatus, comprising: a first intravaginal article assembly module; a second intravaginal article assembly module; and an applicator module capable of receiving and handling applicators suitable for both first intravaginal articles from the first intravaginal article assembly module and second intravaginal articles from the second intravaginal article assembly module. The apparatus only operates with one of the first intravaginal article assembly module and the second intravaginal article assembly module at one time.

In accordance with a third embodiment, there has now been provided a multi-article manufacturing apparatus, comprising: a tampon assembly module; a pessary assembly module; and an applicator module capable of receiving and handling applicators suitable for both tampons from the tampon assembly module and pessaries from the pessary assembly module. The apparatus only operates with one of the tampon assembly module and the pessary assembly module at one time.

In accordance with another embodiment, there has now been provided a method for manufacturing multiple different articles having at least one common component, the method comprising the steps of: providing a plurality of tampons, each of which comprising a first withdrawal member and optionally a first overwrap cover; providing a plurality of pessaries, each of which comprising a second withdrawal member and optionally a second overwrap cover; providing a first plurality of applicators; inserting individual ones of the plurality of tampons into individual ones of the first plurality of applicators; providing a second plurality of applicators; and inserting individual ones of the plurality of pessaries into individual ones of the second plurality of applicators. At least one of the first withdrawal member and the second withdrawal member, the optional first overwrap cover and optional second overwrap cover, and the first plurality of applicators and the second plurality of applicators, with respect to at least one of applicator material make-up, shape, size, and color, is the same.

The present invention also relates to arrays of different articles. In accordance with one embodiment, there has now been provided an array of articles, comprising: a tampon disposed in a first applicator and contained in a first package, the first applicator comprising a barrel, an insertion tip disposed about one end thereof, and a fingergrip disposed about an opposite end thereof; and a pessary disposed in a second applicator and contained in a second package, the second applicator comprising a barrel, an insertion tip disposed about one end thereof, and a fingergrip disposed about an opposite end thereof. The first applicator and the second applicator are the same with respect to at least one of applicator material make-up, shape, size, and color. And he first package and the second package comprise the same brand and/or the tampon and pessary are manufactured by or for the same company.

The present invention further relates to manufacturing methods that utilize an article carrier system wherein the carriers are independently moveable. In accordance with one embodiment, there has now been provided a method of manufacturing intravaginal articles, the method comprising the steps of: providing a plurality of carriers, each of which comprising an interior volume; placing an intravaginal article into the interior volume of one of the plurality of carriers to create filled carriers; transporting the filled carriers to one or more downstream manufacturing steps; and removing the intravaginal articles from the filled carriers to create empty carriers that are available for completing the first step; wherein the carriers are independently moveable.

BRIEF DESCRIPTION OF THE DRAWINGS

The following detailed description of specific embodiments of the present invention can be best understood when read in conjunction with the drawings enclosed herewith.

Figure 1:
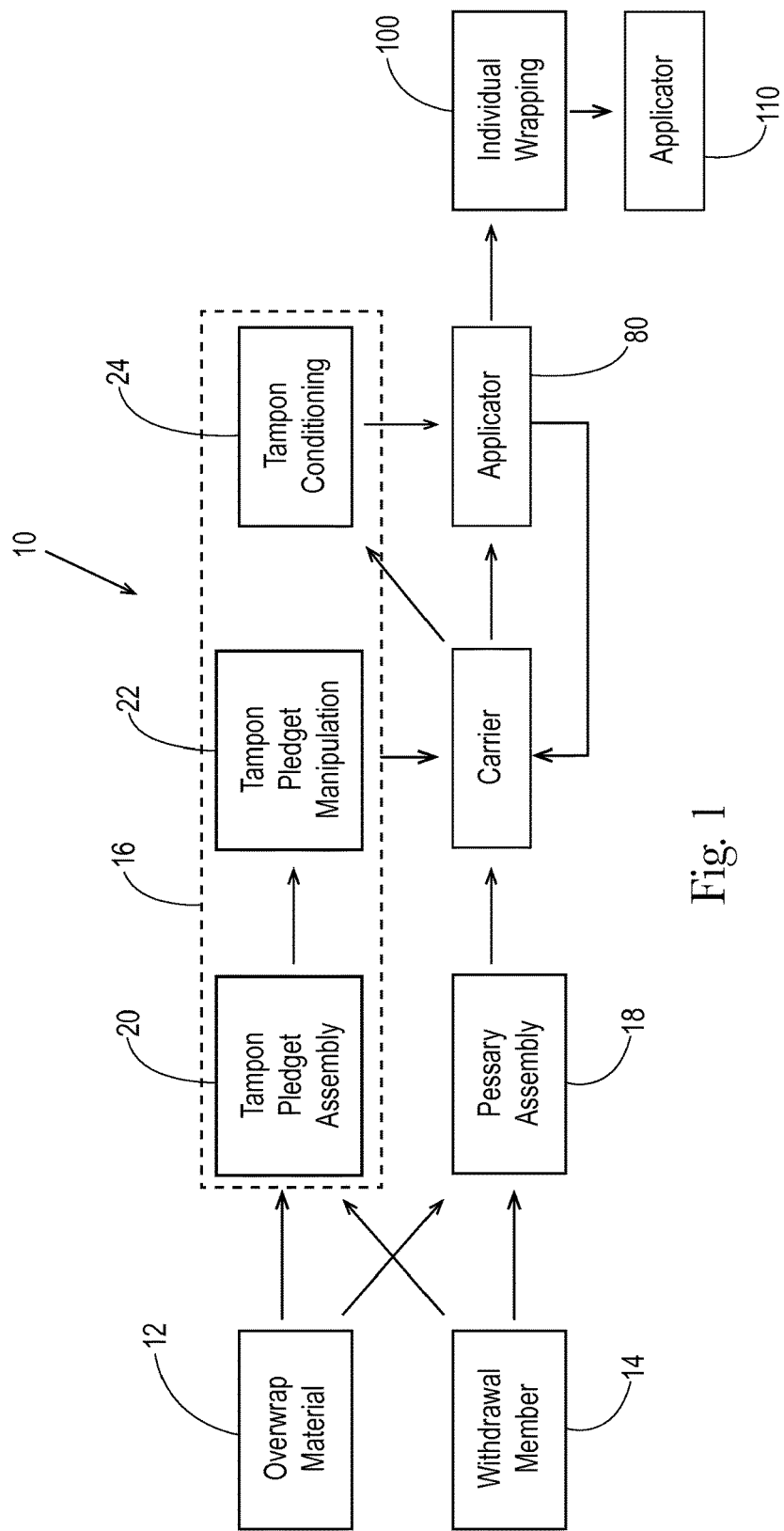
FIG. 1 is a schematic of an exemplary apparatus including various modules.

The embodiments set forth in the drawings are illustrative in nature and not intended to be limiting of the invention defined by the claims. Moreover, individual features of the drawings and invention will be more fully apparent and understood in view of the detailed description.

DETAILED DESCRIPTION OF THE INVENTION

The following text sets forth a broad description of numerous different embodiments of the present invention. The description is to be construed as exemplary only and does not describe every possible embodiment since describing every possible embodiment would be impractical, if not impossible. And it will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential to the present invention unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, the term "intravaginal article" refers to an article or structure suitable for use within the vaginal canal.

As used herein, the term "absorbent article" refers to articles that are designed and configured for absorbing bodily fluids, such as, for example, urine, menses and other vaginal discharge. The absorbent articles are generally capable of absorbing at least 1 gram, 3 grams, 6 grams, or more of bodily fluid. Exemplary absorbent articles include tampons, interlabial products, pantiliners, sanitary napkins, and adult incontinence pads.

As used herein, the term "non-absorbent article" refers to articles that are designed and configured to be placed against/within the body to provide support/pressure to anatomical features and/or to deliver materials (e.g., prebiotics, probiotics, medicaments, etc.). A pessary is one type of non-absorbent article contemplated by the present invention. While the non-absorbent articles are not intended to absorb bodily fluids, some embodiments can absorb and/or capture low amounts of fluid (e.g., less than 1 gram) during use. For example, some pessaries can include an overwrap material and/or contain apertures or hollow portions that may accept available fluid.

As used herein, the term "expanding article" refers to articles that expand via mechanical means or through absorption of a bodily fluid during and/or after insertion into the body.

As used herein, the term "non-expanding article" refers to articles that have substantially the same shape and size after use as they had before use.

As used herein, the term "pessary" refers to any type of substantially non-absorbent (or low absorbent) structure to be placed within the vagina for the purpose of reducing urine leakage and/or supporting a prolapsed uterus and/or bladder. Pessaries can have any variety of shapes and sizes including cylinder, ovate, spherical, tubular, annual rings, "U" shaped, cup shaped, rings, cubes or donut shaped, and can function in any suitable manner, such as, e.g., by direct or indirect application of support, lever force, expansion of the article by selection of material, and/or by inflation of the article.

As used herein, the term "tampon" refers to any type of absorbent structure that can be inserted into the vaginal canal or other body cavity for the absorption of menses and other bodily fluids.

As used herein, the term "pledget" and "tampon pledget" refers to a construction of absorbent material prior to compression or other manipulation into a final tampon form for use by a consumer. A pledget can have a wide variety of shapes, including but not limited to oval, round, chevron, square, rectangular, trapezoidal, and the like.

As used herein, the terms "compression" and "manipulation" refers to the process of pressing, squeezing, compacting or otherwise manipulating the shape, length, width, and/or volume of a material to obtain a tampon form ready for vaginal insertion.

As used herein, "self-sustaining" means the ability to retain its form after compression/manipulation and optional conditioning in the absence of external forces.

As used herein, the term "affixed", "joined" or "attached" as used herein, encompasses configurations in which a first element is directly secured to a second element by affixing the first element directly to the second element, configurations in which the first element is indirectly secured to the second element by affixing the first element to intermediate member(s) which in turn are affixed to the second element, and configurations in which first element is integral with second element, i.e., first element is essentially part of the second element.

The present invention relates to apparatuses for making multiple different articles, including, for example, an absorbent article and a non-absorbent article. An exemplary apparatus 10 is shown in FIG. 1. Apparatus 10 includes an overwrap material supply 12 and a withdrawal member supply 14 that are configured to optionally supply both a tampon (absorbent article) assembly module 16 and a pessary (non-absorbent article) assembly module 18. In this arrangement, while the overwrap material may be the same material makeup or composition, it may be altered before or during the respective article assembly; for example, its size and/or shape may be altered (e.g., by slitting or trimming), and how it is manipulated around the respective article may be different. The overwrap material and withdrawal member supplies can include different sub-supplies for each article, but be controllably routed to the respective article assembly modules through some or all of the same supply equipment. One of ordinary skill in the art should appreciate that an overwrap material may not be employed in either or both of the tampon pledget and pessary making modules. And the same goes for a withdrawal member. The skilled artisan should also appreciate that while the figures herein illustrate a withdrawal member being assembled with a tampon pledget prior to manipulation of the tampon pledget into a final tampon form, some tampon embodiments have their withdrawal member added after the tampon has been fully formed, through, for example, a pierce and loop operation.

Representative overwrap materials include woven fabrics, nonwovens, and flexible films. The fibrous structures can include natural fibers, synthetic fibers, or both. Exemplary fibers include rayon, cotton, bicomponent fibers, polyester fibers polyolefin fibers, and other suitable natural and synthetics fibers known in the art. Suitable flexible films include polyethylene and polypropylene films. When flexible films are used on absorbent articles, the films are generally apertured or otherwise include voids to permit pass through of fluids to be absorbed.

A non-limiting list of suitable withdrawal members includes cords, strings, finger covers, ribbons, and extension of the absorbent material and/or overwrap material. The withdrawal member can optionally be provided with an absorbent member, such as a mass of absorbent material attached to the withdrawal cord. Secondary absorbent members that may be used are described in, e.g., U.S. Pat. No. 6,258,075.

Tampon assembly module 16 includes a tampon pledget making module 20, a tampon pledget manipulation module 22, and a tampon conditioning module 24. Tampon pledget making module 22 generally involves providing a layer of absorbent material, cutting sections of the absorbent material layer into discrete pieces and arranging the piece(s) into a pledget configuration along with some of the overwrap material (optional). Suitable absorbent materials include, but are not limited to, synthetic fibers, natural fibers, foams, and absorbent gelling material. The natural fibers may include, for example, cotton, wood pulp, flax, hemp, and rayon. Rayon fibers can have a variety of cross-sectional shapes, such as, for example, round and tri-lobal. The synthetic fibers can include, but are not limited to, polyester, polyolefin, nylon, polyethylene, polypropylene, polyacrylic, cellulose acetate, vinyl polyacetate, bicomponent fibers, and mixtures thereof. The pledget configuration may be a single piece of the absorbent material in a generally flat configuration, multiple pieces of the absorbent material in a stacked configuration (periphery of the stacks coterminous or not), one or more pieces of the absorbent material rolled or folded up, and other configurations that are known by one of ordinary skill in the art. In some embodiments, the tampon pledget making process includes associating a withdrawal member with the tampon pledget; for example, by sewing a withdrawal member to the piece(s) of absorbent material, or by looping through or around the piece(s) of absorbent material prior to compression or other pledget manipulation.

Figure 2:
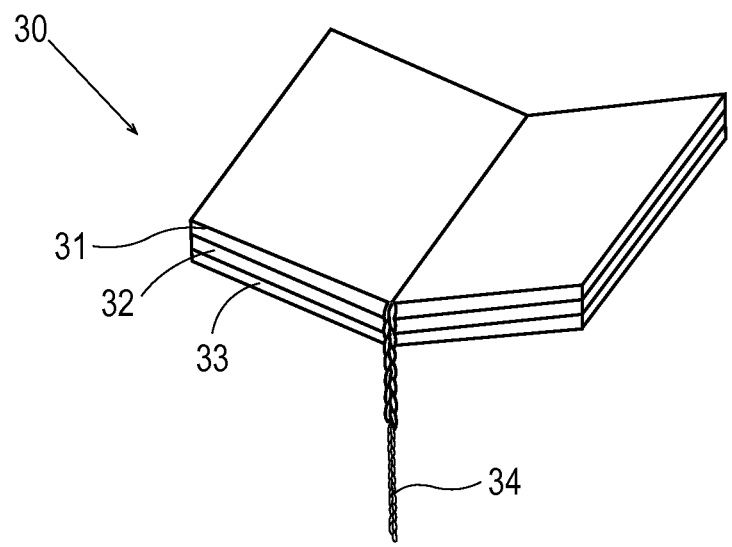
FIG. 2 is perspective view of an exemplary tampon pledget.

An exemplary tampon pledget 30 is shown in FIG. 2. Tampon pledget 30 is shown having 3 layers 31, 32, and 33 of absorbent material comprising cotton and rayon fibers. A withdrawal member 34 is affixed to and extends from one end of the pledget.

Figure 3:
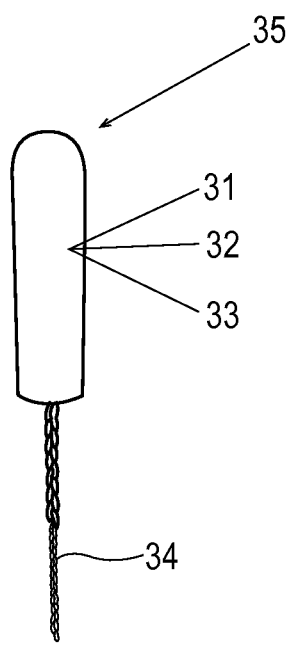
FIG. 3 is side view of the tampon pledget of FIG. 2 after its compression/manipulation.
Figure 4:
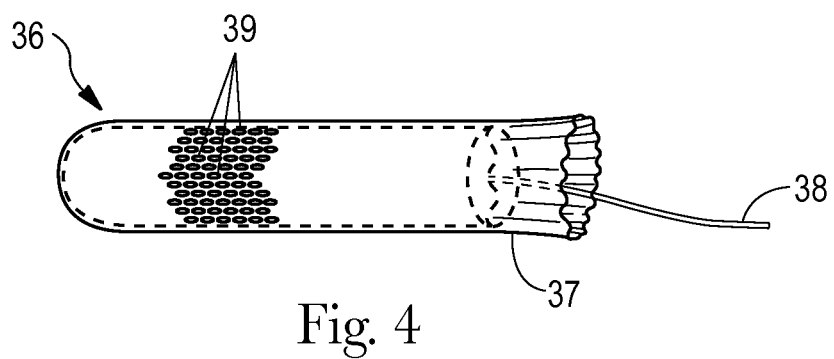
FIG. 4 is a side view of an exemplary tampon comprising an optional overwrap material.

Referring again to FIG. 1, tampon manipulation module 22 generally involves changing the size and/or shape of the tampon pledget into a tampon final form. Tampon pledgets typically are folded and/or compressed within a tampon mold to a generally cylindrical geometry to facilitate comfortable insertion into the body. The folding and compression can be done, for example, axially (lengthwise), radially (widthwise), or both. FIG. 3 shows the tampon pledget 30 from FIG. 2 in a compressed and shaped final tampon 35 configuration. FIG. 4 shows another exemplary tampon 36 that includes an optional overwrap 37 and withdrawal member 38. Overwrap 37 includes fluid pathways 39 to render the overwrap liquid permeable. The skilled artisan should appreciate that while overwrap 37 is shown as extending beyond the tampon absorbent body in FIG. 4, that other amounts of coverage and configuration can be employed.

FIG. 1 includes an optional tampon conditioning module 24 as part of the tampon assembly 16. Once tampon pledgets have been compressed/manipulated to a final form, they may require conditioning to temporarily maintain this self-sustaining form prior to insertion into the vagina so as not to expand substantially prior to absorbing bodily fluids. Conditioning can comprise application of energy to a manipulated tampon pledget. For example, steam, heat, microwave energy can be applied to the manipulated tampon pledget to help hold its form. The conditioning can take place within a tampon mold during or after its manipulation, or be done separately from the compression/manipulation step. Exemplary conditioning methods are disclosed in U.S. Pat. No. 7,947,608 and U.S. Patent Application Publication No. 2005/0027275.

Exemplary apparatus 10 in FIG. 1 includes a pessary assembly module 18. The pessary assembly module can include numerous operations. By way of example only, pessary assembly module can include supplying pessary bodies and attaching a withdrawal member and/or an optional overwrap material to the pessary body. The pessary assembly module can also include constructing a pessary body from component body parts that are molded or otherwise separately manufactured (e.g., the pessary body can be constructed from two or more injection molded pieces that can snap together to form a continuous shell). Pessary bodies can be made from a variety of materials, including plastic, foam (closed cell and open cell), rubber, silicone, fibrous materials, metals, and combinations thereof. The pessary bodies can be formed in any suitable manner, such as, for example, using injection molding or blow molding techniques. A pessary body can also be made from fibrous materials. The fibrous materials may be hydrophilic or hydrophobic in nature. The fibrous materials can be the same as that employed in tampons, wherein the fibrous materials are either densified significantly to render the pessary body substantially non-absorbent or are covered with a material to inhibit/prevent absorption of bodily fluids. For example, pessary assembly module 18 can employ the absorbent materials used in tampon assembly module 16 and then cover the same with an overwrap material (e.g., a non-apertured polymeric film) that is essentially fluid impermeable. The pessaries assembled in module 18 may be expandable or non-expandable. A variety of pessary designs are disclosed in U.S. Pat. Nos. 6,808,485 and 8,217,219; and U.S. Patent Publication Numbers 2002/0120243, 2011/0152604, 2011/0160525, 2012/0136199, 2012/0165599, 2012/0165601, 2012/0217068, and 2013/0158340.

Figure 5A:
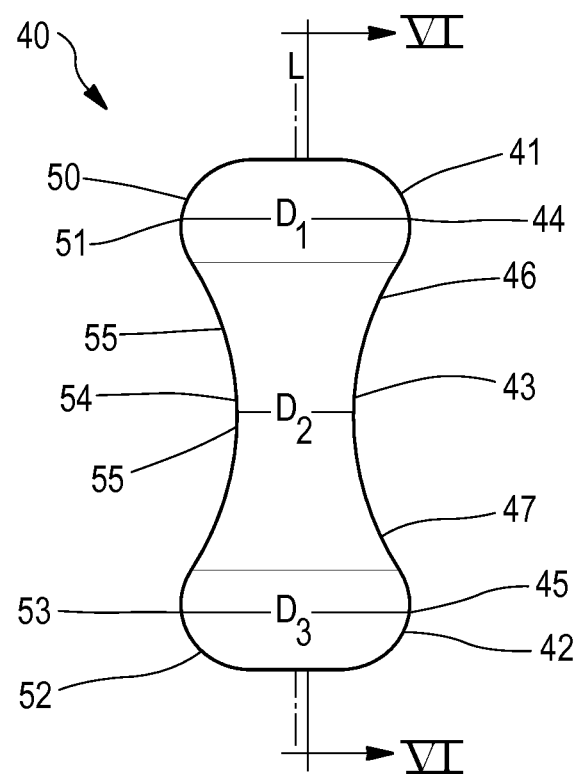
FIG. 5A is a side view of an exemplary pessary.
Figure 5B:
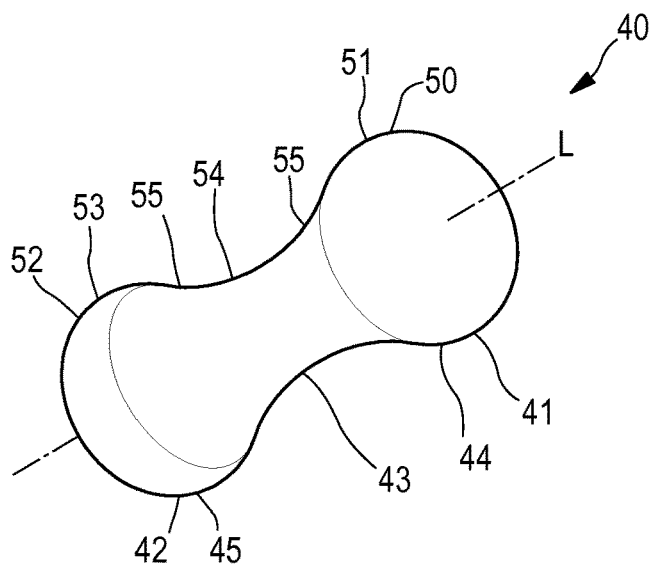
FIG. 5B is a perspective view of the pessary shown in FIG. 5A.

FIGS. 5A and 5B illustrate an exemplary pessary 40. Pessary 40 includes a pessary body having an upper portion 41, a lower portion 42, a middle portion 43, a pressure region 44 of the upper portion 41, a pressure region 45 of the lower portion 42, a maximum diameter $D_1$, a minimum diameter $D_2$, a slope 46 extending from the upper portion 41 to the middle portion 43, a slope 47 from the middle portion 43 to the lower portion 42, a longitudinal axis (L) and a transverse axis (T). Pessary 40 can have a top 50 that includes a convex portion 51, a base 52 that includes a convex portion 53, and sides 54 that include concave portions 55. The pessary can be symmetric about the longitudinal axis, including for example, wherein the base is circular and symmetric about the longitudinal axis. The pessary can include a third diameter $D_3$ that is greater than minimum diameter $D_2$, and convex portion 51 can be aligned with maximum diameter $D_1$ to provide pressure region 44, and convex portion 53 can be aligned with maximum diameter $D_3$ to provide pressure region 45.

Figure 6:
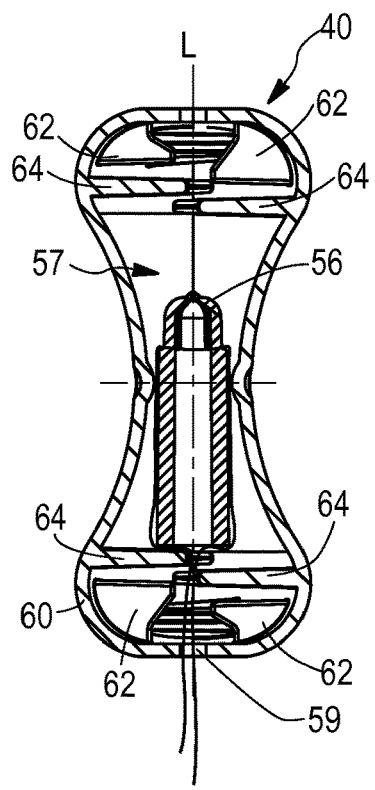
FIG. 6 is a cross-sectional view of the pessary as taken through line VI-VI in FIG. 5A.

FIG. 6 shows a cross section of pessary 40 taken along line VI-VI of FIG. 5A. Pessary 40 includes a number of features that facilitate receipt and retention of a withdrawal cord anchor 56. Pessary 40 includes an interior region 57 that is hollow. Pessary 40 can have an aperture 58 through any surface of the pessary body—aperture 59 is shown extending through lower portion 60 in FIG. 4. The interior region 57 of pessary 40 can include one or more inwardly extending protuberances. Hollow region 57 can have a first pair of protuberances 62 and a second pair of protuberances 64. The first pair of protuberances 62 can extend from an end of the pessary body towards the second pair of protuberances 64. The second pair of protuberances 64 can extend parallel the aperture at the end of the pessary and be flexible. The second pair of protuberances 64 allow withdrawal cord anchor 56 to move past them when inserted through the aperture 59. Once the withdrawal cord anchor 56 has passed the second pair of protuberances 64, the first set of protuberances 62 prevent the second pair of protuberances 64 from bending towards aperture 58 thereby maintaining the withdrawal cord anchor 56 inside hollow region 57.

Figure 7:
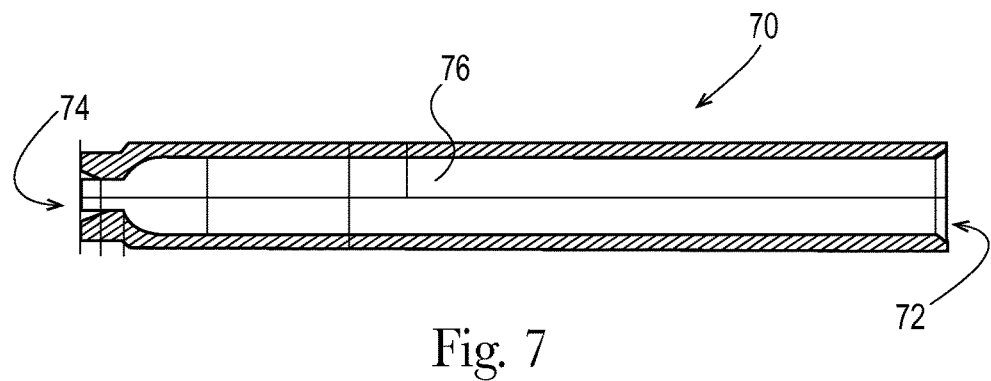
FIG. 7 is a cross-sectional view of an exemplary carrier provided by the present invention.

Referring again to FIG. 1, tampons and pessaries are transferred from their respective assembly modules into a carrier associated with carrier module 69. The carriers can be a tubular member that has a hollow interior sized and configured to receive the tampons and pessaries. A cross-sectional view of an exemplary carrier 70 is shown in FIG. 7. Exemplary carrier 70 includes a first end 72 for receiving a tampon or pessary, an opposing end 74, and a hollow interior portion 76. The exterior portion of end 74 comprises features to facilitate handling carrier 70. The carriers can be made from numerous materials, including, for example, plastics, cardboard, metals, and combinations thereof. In some embodiments, the carriers are independently moveable, meaning that they can be moved from one module or location to a downstream manufacturing module or location while not being permanently affixed to any portion of the apparatus. For example, multiple carriers can be placed next to one another on a belt and maintain their position simply by an adjacent carrier or flight on the belt. As noted above, the tampons can optionally be conditioned with a microwave source. When this process step is employed, having a carrier that is made from a non-metal material (e.g., a polyester thermoplastic material) and that is independently moveable permits the carriers to be successfully routed through a microwave conditioning apparatus.

Figure 8:
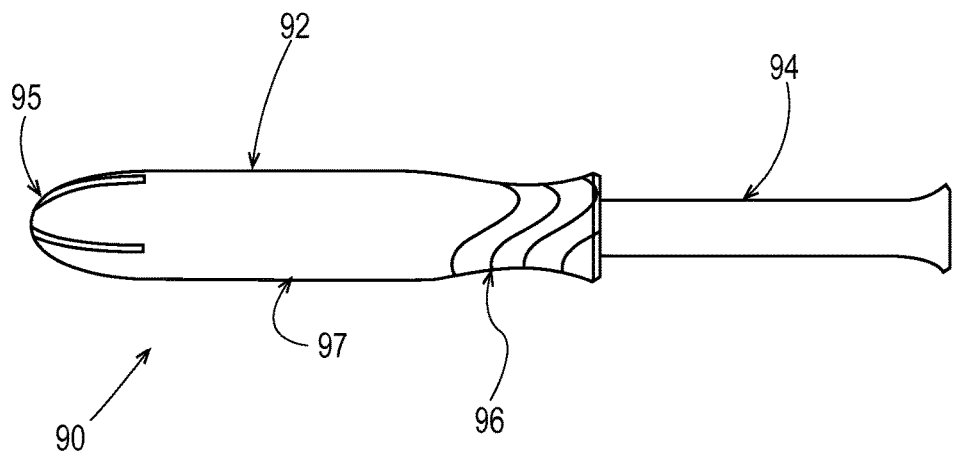
FIG. 8 is a side view of an exemplary intravaginal article applicator.

Referring again to FIG. 1, carriers containing a tampon or pessary are routed to applicator module 80 wherein the intravaginal article is transferred from a carrier and into an applicator. Applicators for inserting intravaginal articles into the body are well known. An exemplary applicator 90 is shown in FIG. 8. Applicator 90 comprises an insertion member 92 that houses an intravaginal article and that is inserted into the body, and a plunger 94 that is moved to expel the intravaginal article from insertion member 92. Insertion member 92 is shown having an insertion tip 95, a fingertip 96, and a barrel portion 97 disposed between tip 95 and fingergrip 96. Applicators are generally made from cardboard or plastic according to various methods known by those of ordinary skill in the art. Applicator module 80 may be configured to accept either a single size/geometry applicator or two more different size/geometry applicators.

Figure 9:
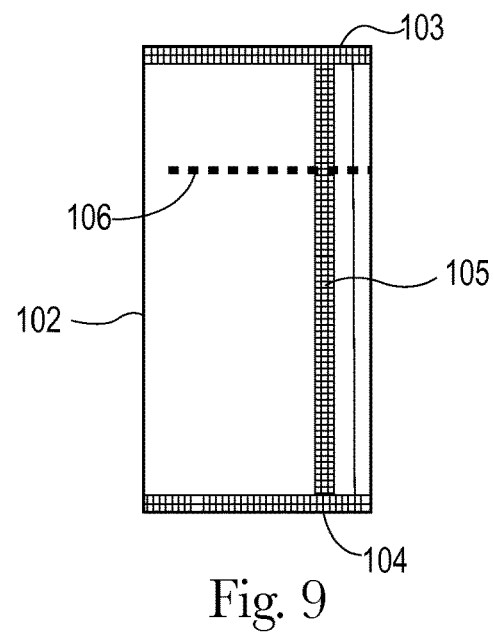
FIG. 9 is a side view of an exemplary wrapper for individually wrapping an intravaginal article.
Figure 10:
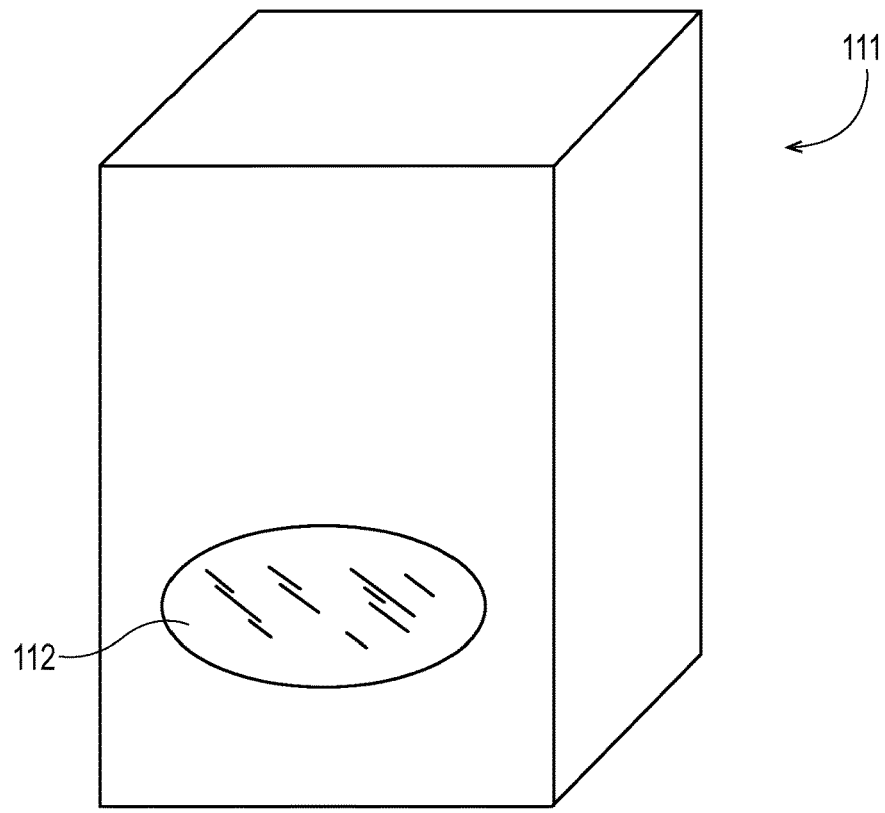
FIG. 10 is a front perspective view of an exemplary package suitable for containing a plurality of individual-wrapped intravaginal articles.

Referring once more to FIG. 1, applicators containing an intravaginal article are routed to a wrapper module 100 wherein individual applicators are wrapped for cleanliness and portability. Suitable wrapping materials include, but are not limited to, paper, coated paper, polymeric films, nonwovens, and combinations thereof. FIG. 9 illustrates an exemplary wrapper 102 in the form or a tube or sleeve of material having two end seals 103 and 104, a side seal 105, and a perforation 106 to facilitate opening of wrapper 102. Several of the individually-wrapped applicators are then packaged at packaging module 110 into a secondary package, such as, for example, a bag or carton. An exemplary package 111 is shown in FIG. 10. Package 111 includes a window 112 for viewing some of the individually-wrapped articles.

As shown in FIG. 1, after tampons or pessaries are transferred from the carriers to applicators, the carriers are recirculated back upstream to be available for receiving additional tampons and pessaries from their respective assembly modules.

In one embodiment, only one of the tampon assembly module 16 and the pessary assembly module 18 operates at a given time. This allows distinct applicators, wrappers, and/or packages to be employed for the final tampon and pessary articles. However, the two assembly modules can alternatively operate simultaneously wherein the final tampon and pessary articles are placed in the same applicator and then routed to separate wrapping and packaging modules (not shown). Finally, the two assembly modules can operate simultaneously wherein controls systems are used to coordinate distinct applicators, wrappers, and packages for the final tampons and pessaries.

Figure 11:
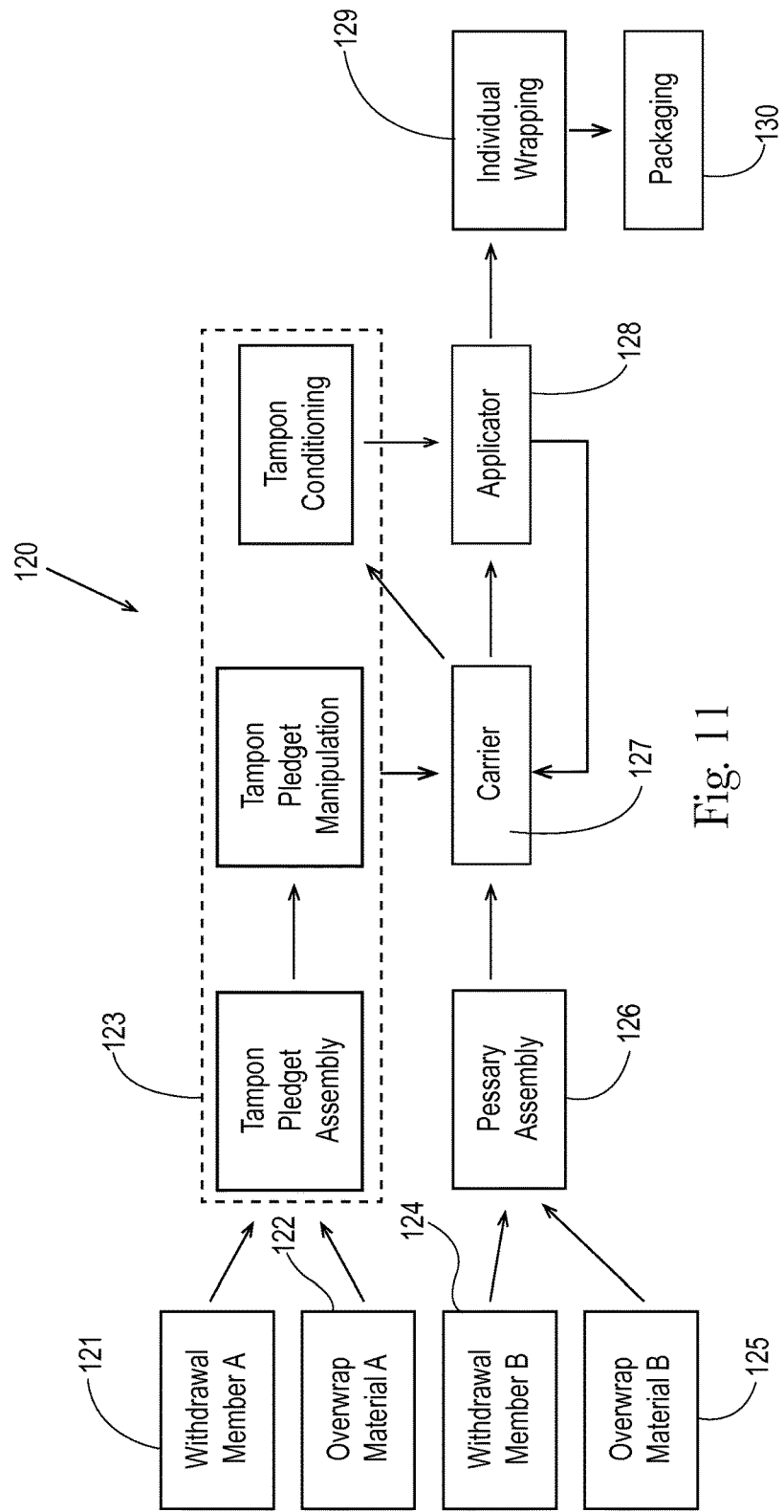
FIG. 11 is a schematic of a second apparatus embodiment of the present invention.

FIG. 11 shows another exemplary apparatus of the present invention that employs a separate overwrap material supply and withdrawal member supply for each of the tampon assemblies and pessary assemblies. Apparatus 120 includes a withdrawal member supply 121 and overwrap material supply 122 for tampon assembly module 123, and a withdrawal member supply 124 and overwrap material supply 125 for pessary assembly module 126. Apparatus 120 also includes carriers 127, an applicator module 128, a wrapper module 129, and a packaging module 130.

Figure 12:
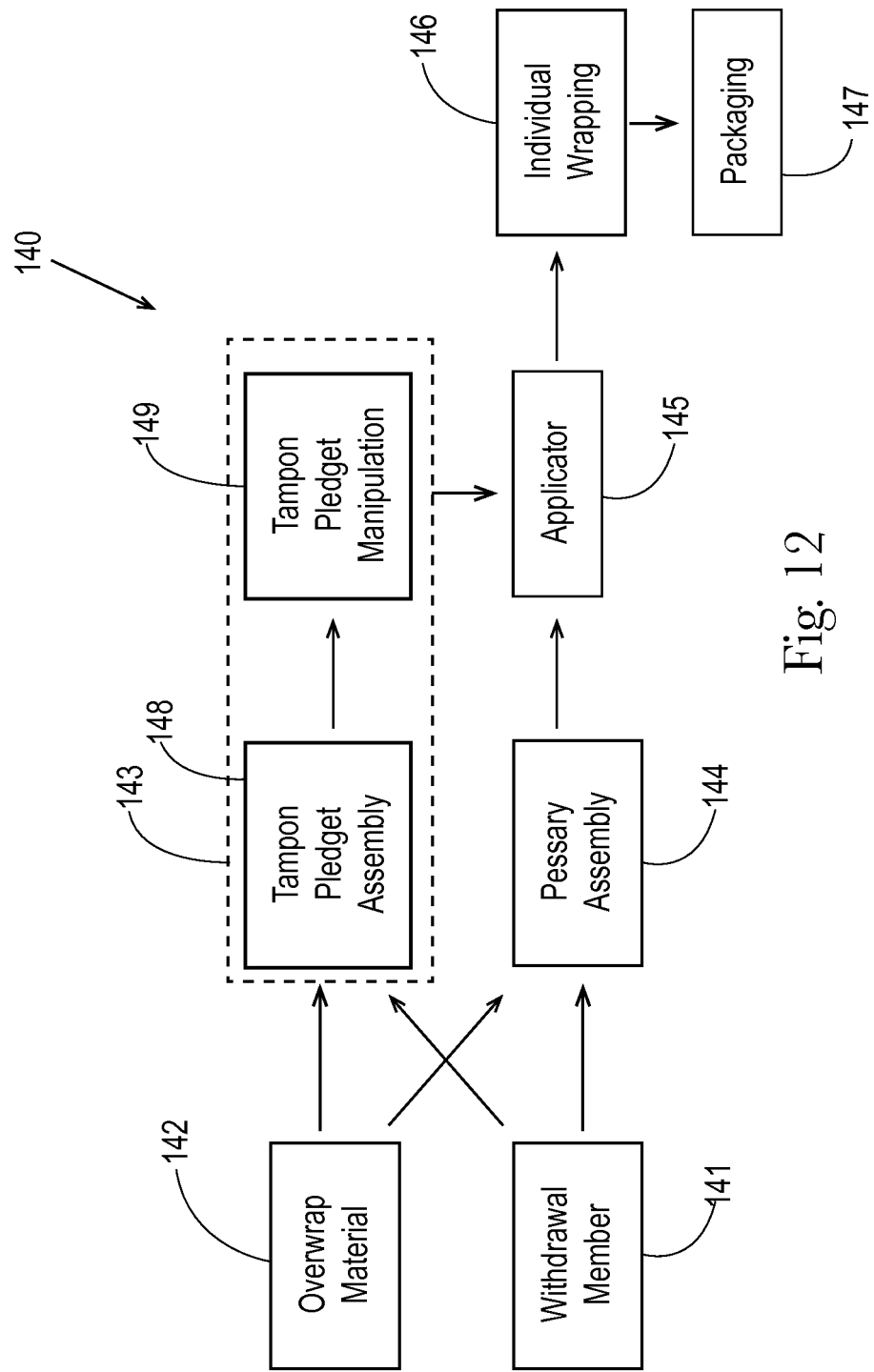
FIG. 12 is a schematic of a third apparatus embodiment of the present invention.

FIG. 12 shows yet another exemplary apparatus 140 of the present invention that is similar that shown in FIG. 1, but does not include a carrier system. In this embodiment, a compressed or otherwise manipulated tampon and a pessary article are transferred into applicators without being placed into an interim temporary holding structure such as a carrier or the like. Apparatus 140 includes a withdrawal member supply 141, an overwrap material supply 142, a tampon assembly module 143, a pessary assembly module 144, an applicator module 145, a wrapper module 146, and a packaging module 147. Tampon assembly 143 includes a tampon pledget making module 148 and a tampon pledget manipulation module 149.

Apparatuses and methods of the present invention can be employed to manufacture an array of articles. The article arrays can include a number of different combinations of articles, including, for example, an absorbent article and a non-absorbent article, an expandable article and a non-expandable article, a first type of intravaginal article, and a second type of intravaginal article, a tampon and a pessary, a first fibrous article and a second fibrous article, and the like. The arrays can comprise two or more different articles. The different articles and/or applicators for inserting the same can comprise some components/raw materials that are the same. The different articles within the array can be manufactured by or for the same company and/or comprise the same marketing aspects, including, for example, brand names and other brand equity aspects.

Figure 13:
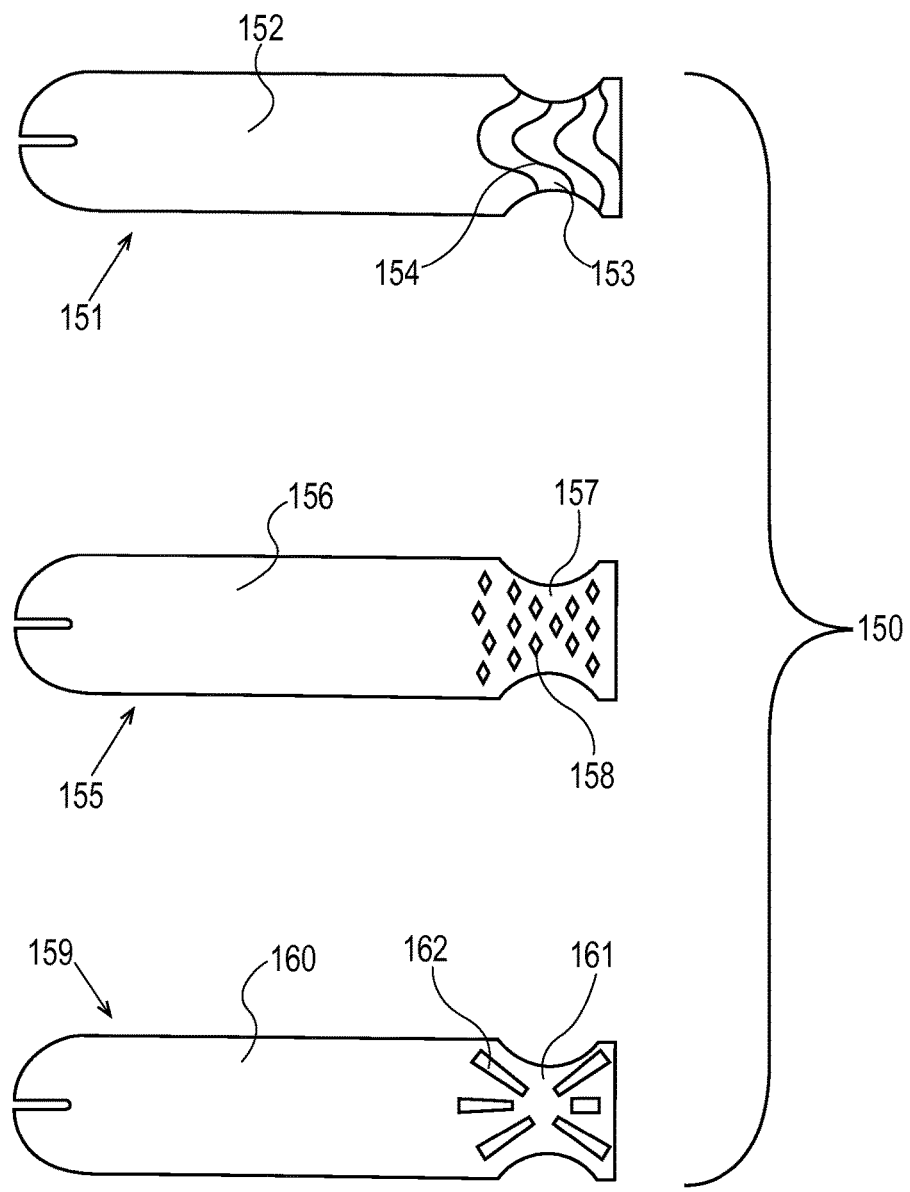
FIG. 13 is a side view of an array of applicator components associated with an array of different intravaginal articles.

In one embodiment, the article array comprises a first applicator containing a tampon and second applicator containing a pessary. Each of the tampon and the pessary comprises a withdrawal member and an optional overwrap material. A common component in the array can be any one or more of the applicator, the withdrawal member, and the overwrap material. The first and second applicators can be the same with respect to their size and shape of the applicator barrel and/or the size and shape of the insertion tip. And the first and second applicators may be the same with respect to their material make-up. The first and second applicators may be the same except for a design of their fingergrips, their color (including different hues and shades), or both. By way of example only, FIG. 13 shows an array 150 of applicator insertion members, comprising a first applicator insertion member 151 that includes a first color 152 and first fingergrip design 153 having first gripping elements 154, a second applicator insertion member 155 that includes a second color 156 and a second fingergrip design 157 having second griping elements 158, and a third applicator insertion member 159 that includes a third color 160 and a third fingergrip design 161 having third gripping elements 162.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-article manufacturing apparatus, comprising:
   (a) a first intravaginal article assembly module;
   (b) a second intravaginal article assembly module; and
   (c) an applicator module capable of receiving and handling applicators suitable for both first intravaginal articles from the first intravaginal article assembly module and second intravaginal articles from the second intravaginal article assembly module;
   (d) wherein the apparatus only operates with one of the first intravaginal article assembly module and the second intravaginal article assembly module at one time; and
   (e) wherein the first intravaginal articles are absorbent articles and the second intravaginal articles are non-absorbent articles.

2. The apparatus of claim 1, wherein the second intravaginal articles are non-expanding articles.

3. The apparatus of claim 1, wherein the second intravaginal articles are expanding articles.

4. The apparatus of claim 1, wherein both the first intravaginal articles and the second intravaginal articles comprises natural fibers, synthetic fibers, or mixtures thereof.

5. A multi-article manufacturing apparatus, comprising:
   (a) a tampon assembly module;
   (b) a pessary assembly module; and
   (c) an applicator module capable of receiving and handling applicators suitable for both tampons from the tampon assembly module and pessaries from the pessary assembly module;
   (d) wherein the apparatus only operates with one of the tampon assembly module and the pessary assembly module at one time.

6. The apparatus of claim 5, further comprising (e) a wrapper module for individually wrapping applicators containing tampons or pessaries.

7. The apparatus of claim 6, further comprising (f) a packaging module for packaging together a plurality of individually wrapped applicators containing tampons or pessaries.

8. The apparatus of claim 5, further comprising (g) a plurality of carriers that are independently moveable, each of the plurality of carriers being capable of transporting individual tampons and individual pessaries from the respective assembly modules to the applicator module.

9. The apparatus of claim 8, further comprising (h) a plurality of pistons each of which pushes an individual tampon or pessary from a carrier and into an applicator at the applicator module.

* * * * *